United States Patent [19]

Kawahara et al.

[11] 4,439,153
[45] Mar. 27, 1984

[54] BIO-FUNCTIONAL DENTURE

[75] Inventors: Haruyuki Kawahara, Moriguchi; Nobuhiro Ishizaki, Uozakikitamachi; Hiroki Wada, Suita, all of Japan

[73] Assignee: Wada Seimitsu Shiken Kabushiki Kaisha, Osaka, Japan

[21] Appl. No.: 450,751

[22] Filed: Dec. 17, 1982

[51] Int. Cl.$^3$ .............................................. A61C 13/00
[52] U.S. Cl. .................................................. 433/200
[58] Field of Search .................................. 433/9, 200

[56] References Cited

U.S. PATENT DOCUMENTS 1,945,767  2/1934  Bergerhausen et al. ............ 433/200
4,165,561  8/1979  Miller et al. ............................ 433/9

Primary Examiner—Robert Peshock
Attorney, Agent, or Firm—Koda and Androlia

[57] ABSTRACT

This disclosure relates to a denture having a porous metal gauze as a denture plate formed of plural wire nets with a straight wire used as warps and wefts. The nets are laid one over another in layers in the manner that the meshes thereof are staggered each other with respect to the direction of thickness and the crossing portions of the warps and wefts in the same plane and the crossing portions of the warps and wefts in contact with each other in the direction of thickness are sintered to have a plurality of minute and complicatedly curved pores in the porous metal gauze. The denture permits penetration of saliva and food liquid through the thickness of the denture plate to supply oxygen and nutrient to the mucous membrane under the plate to thereby maintain physiological function and health of the membrane and to provide a sense of wearing the denture and a sense of bite occlusion in such a natural state as would hardly be brought about by a conventional denture.

7 Claims, 9 Drawing Figures

BIO-FUNCTIONAL DENTURE

BACKGROUND OF THE INVENTION

1. Field of the Invention

This invention relates generally to a denture structure, and more particularly to a denture having a porous metal gauze as a denture plate including a full and partial denture.

2. Prior Art

Two types of denture plate in the form of a resin plate and a metal plate having heretofore been available as a denture plate which is designed to make it possible for the denture plate to have a suction effect on the mucous membrane tissue as of the palate region and alveolus region under the denture plate, and it is demonstrated that the metal plate is superior in many respects to the resin plate. Alloy metals, such as gold alloy, platinum alloy, cobalt chromium, nickel chromium, which are biologically unharmful are selected as a material adapted for use in metal plate and are formed into a solid plate by casting or coining. Since the metal plate is higher in strength than the resin plate, it has the advantage that the metal plate can be formed thin to such a degree that the user of the denture is relieved of a disagreeable feeling due to the presence of a foreign substance in the mouth; that it is free from damage or deformation due to long time use; and that it is small in volume change. On the other hand, the metal plate has the counterbalancing disadvantage that, since the mucous membrane as of the palate and alveolus regions under the denture plate is blocked to passage of the liquid in the mouth to thereby cut off the supply of oxygen and nutrient and produce adverse effects on the physiological and biological functions of the membrane; that the user of a denture is prevented from enjoying his sense of taste for food and perception of food temperature in a natural state approximate to what would be brought about without the denture put in; and that the stiff solid plate gives a sense of something foreign to the mouth during biting. These are some of the problems for further improvement.

SUMMARY OF THE INVENTION

This invention is directed to the solution of the problems described above. A primary object of the invention is to provide a denture having a denture plate formed of a porous metal gauze. The porous metal denture plate has the advantage that saliva passes through the thickness of metal plate and makes free communication between the underside surface of the plate which faces the mucous membrane and the upside of the plate which faces the oral cavity to thereby supply the mucous membrane tissue with nutrient for the maintenance of physiological passage of air through the denture plate is blocked by the surface tension of saliva to maintain a sucking effect on the mucous membrane surface and to prevent the denture from coming off from the mucous membrane, thus making it possible to sense the temperature and taste of food taken in a substantially natural state; that since the denture plate permitting reduction in weight in a greater degree than that of the conventional denture plate made of a solid plate not only relieves the user of the unnatural feeling aroused by the denture put in but also is large in the range of elastic deformation with respect to bite occlusion force, the user is given a greater refreshing sense of bite occulsion; and that in addition, the plate permits the passage of saliva but prevents the leavings of masticated food from going deep into the thickness of the plate and allows them to stay in the surface area in a degree sufficient to permit removal of the leavings from the plate by cleaning, for example, during sleep of the user.

The object described above can be achieved by the application of a denture plate of a porous metal gauze. The denture plate is made of a sintered porous metal plate produced in such a manner that a metal wire is used as a warp and a weft to be made into a thin wire set and the nets obtained are laid one over another in layers and pressed so as to sinter the portions of warps and wefts crossing each other in the same plane and those of warps and wefts in contact with each other in the direction of thickness. The crossing portions described will hereinafter be referred to simply as "crossing portions." The warps and wefts forming the porous metal plate provided with pores of 0.1 to 500 $\mu$m are staggered with each other with respect to the direction of thickness (i.e. the warps and wefts in the lower layer are staggered with respect to those in the upper layer in the direction of extent of the wire net produced), while they are held substantially horizontal to each other with respect to the direction of the wire net produced. Accordingly, the denture plate of wire net thus made of warps and wefts makes it possible to hold a stretch of film which permits penetration of saliva and food liquid with respect to the direction of thickness of the denture plate but which prevents the passage of air through the pores by the surface tension of saliva, thus preventing the leavings of masticated food from going deep into the depths of the plate by the warps and wefts staggered in the direction of thickness of the plate. The denture plate substantially uniformly provides the function of the pores over its entire area by the parallel relation of warps and wefts with respect to the direction of extent of the plate and can make larger elastic deformation than the conventional denture plate when a biting occlusion force is applied.

The above and other objects and advantages of the invention will become more apparent from a description given below of preferred embodiments of the invention in conjunction with the accompanying drawings.

DETAILED DESCRIPTION OF THE INVENTION

Figure 1:
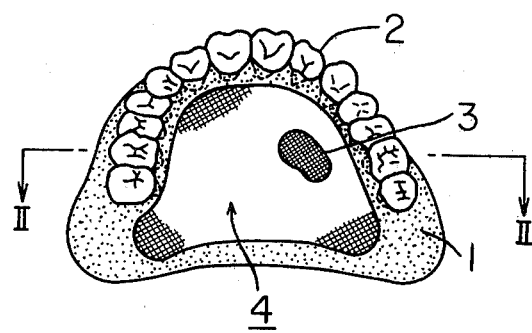
FIG. 1 is a perspective plan view of a full denture of the upper jaw embodying the invention.
Figure 2:
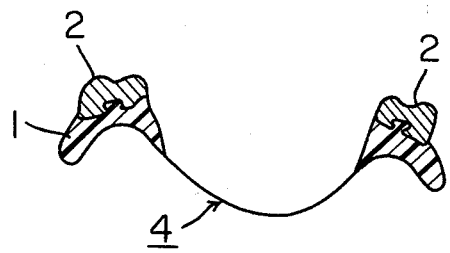
FIG. 2 is an enlarged sectional view taken along the line II—II of FIG. 1.
Figure 5:
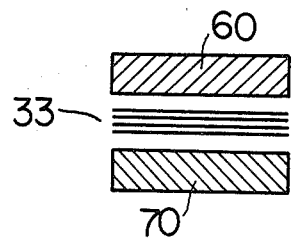
FIGS. 5 and 6 show procedures for making a denture plate according to the invention.
Figure 6:
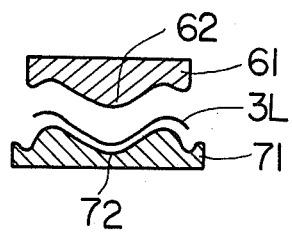
Figure 7:
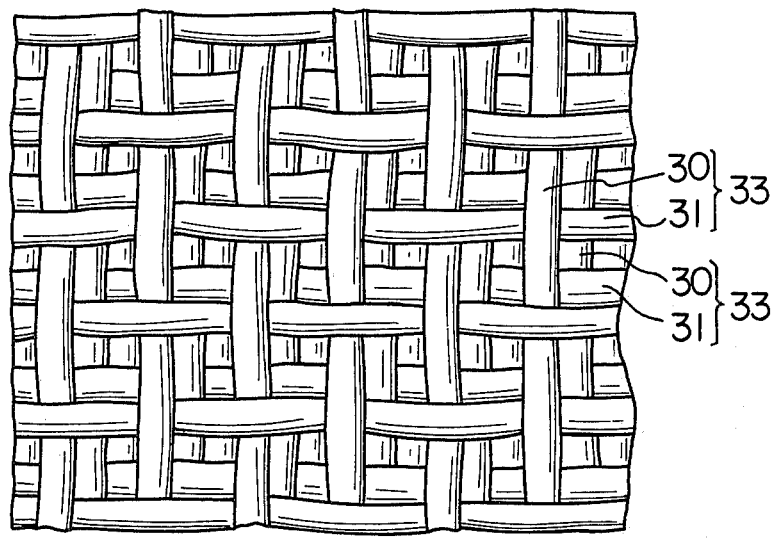
FIG. 7 is a segmentary enlarged microscopic plan type view showing the melting of the denture plate.
Figure 9:
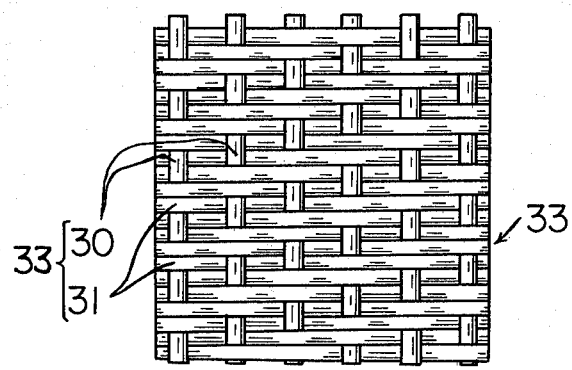
FIG. 9 is a view similar to FIG. 7 showing the netting of the denture plate according to another embodiment of the invention.

In the embodiment shown in FIGS. 1 and 2, the numeral 1 designates an alveolar ridge of a resin denture plate and 3 designates a porous metal gauze connected to the resin ridge 1 over the entire circumferential edge of the denture plate. The alveolar ridge 1 and the metal gauze 3 constitute a denture plate 4. The numeral 2 designates artifical teeth. The porous metal gauze 3 used in the invention, as shown in FIGS. 7 and 9, is a sintered netting body. The body is made in the manner that a linear metal wire is used as a warp 30 and a weft 31 to form a thin metal net 33, a plurality of the nets are laid one over another so as to permit meshes 32 to stagger each other with respect to the direction of thickness of the net and to permit the warps 30 and wefts 31 to be substantially parallel to each other with respect to the extent of the net and are pressed in the direction of thickness, and the crossing portions 300 of warps 30 and wefts 31 extending in the same plane and the crossing portions 301 of warps 30 and wefts 31 placed in contact with each other in the direction of the thickness of the net are sintered so as to form therein a plurality of minute and complicatedly curved pores 34 through the thickness of the net. In the embodiment shown in FIG. 7, the texture of nets 33 is shown in the case of plain square weave, and in the embodiment shown in FIG. 9, the texture of nets 33 is shown in the form of twilled Dutch weave. Although not shown, any texture other than the textures shown above may be employed. As the warps 30 and wefts 31 may be used those titanium alloy, cobalt chromium alloy, stainless steel alloy which have heretofore been used for a metal denture plate and other metal materials which are biologically unharmful. The thickness of one piece of net 33 measures, for example, about 0.1 to 0.2 mm in the case of plain square weave, and about 0.1 to 0.3 mm in the case of twilled Dutch weave. A combination of about 7–8 layers of nets of one or several kinds of the above waves (but the surface layers is preferably formed of twilled Dutch weave) is formed to have a total thickness of about 0.4 mm (400 $\mu$m) after pressing and sintering. But depending upon circumstances, it is possible to change the types of weave and the number of nets and increase or decrease the total thickness in the range of 100 to 1000. The warp 30 and weft 31 having a diameter of 60 to 120 $\mu$m are most widely used, but it may not be objectionable to dispose large diameter warps and wefts in the center and smaller diameter ones in the other portions of the net for the purpose of maintaining the strength of the net. For clear understanding of the structure of the porous metal gauze 3, a description will be given below of the gauze with reference to procedures for producing the gauze 3. As shown in FIG. 5, plural sheets of wire nets 33 are inserted in layers between a pair of upper mold 60 and lower mold 70. The molds 60 and 70 are closed and pressed under a pressure of 0.1 to 100 kg/cm$^2$ and is heated in a non-oxidous atmosphere, for example, in vacuo or in reduced gas atmosphere in the range of temperatures higher than a recrystallization temperature of alloy of the wire net 33 and below a temperature of melting point MP to obtain a wire net 3L sintered in layers. In the above layered net, the meshes 32 of the metal wire net 33 are disposed in the manner that the warps 30 and wefts 31, namely the meshes 32, in the upper and lower layers, are staggered each other with respect to the direction of thickness of the metal wire 33 and are substantially parallel to each other with respect to the direction of extent of the metal wire 33. When the layered nets 33 are different in texture, for example when the uppermost layer is of twilled Dutch weave and all the layers thereunder are of plain square weave, the nets of plain square weave must positively be brought into a staggered relation with each other, but since the net 33 of the twilled Dutch weave in the uppermost layer and the net 33 of the plain square weave thereunder are different in mesh 32 from each other, they can be brought into a mutually staggered relation without positively staggering the nets 33. In order for the layered and sintered wire net 3L thus obtained in succession to the above first procedure to have a curved surface necessary for the denture plate, the wire net 3L is inserted and pressed between the upper and lower molds 61 and 71 having a convex portion 62 and a concave portion 72 respectively formed in an opposed relation with each other. The molds 61 and 71 are separated to release the pressed wire net 3L from the molds to obtain the porous metal gauze 3 of the invention having necessary concave and convex shapes as shown in FIG. 6. The metal gauze 3 obtained in layers by the pressure and heating has the following characteristics.

Figure 8:
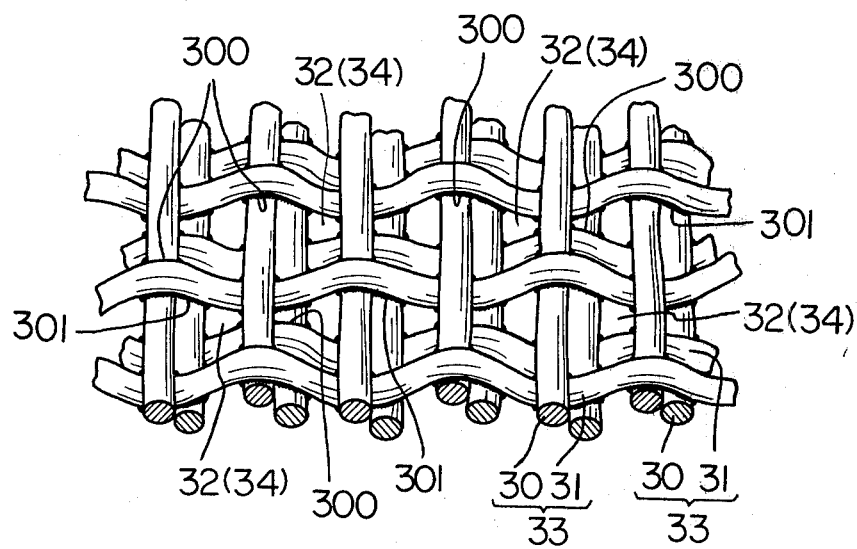
FIG. 8 is a segmentary enlarged microscopic perspective type view.

FIG. 7 shows in a microscopic type of network structure (weave structure) of a denture plate 4 made of a porous metal gauze 3. As shown, the warps 30 and wefts 31 are arranged such that meshes 32 are staggered each other with respect to the direction of thickness of the net and are substantially parallel with respect to the direction of extension of the net and that the crossing portions 300 of the warps 30 and wefts 31 in the same plane and the crossing portions 301 of the warps and 30 and wefts 31 in contact with each other in the direction of thickness of the net are respectively sintered. As a result, the meshes 32 do not form linear gaps with respect to the direction of thickness, but are discontinued by warps and wefts staggered in position and form a series of minute gaps 34 in a variously curved shape. On the other hand, the opening degree of meshes 32 within a unit area is substantially uniform in any portion with respect to the direction of extent over the entire surface of the denture plate 4 by parallel arrangement of the meshes 32. The porosity (i.e. space factor of pore 34) in the denture plate 4 is on the order of 20 to 70%. The diameter of the pore 34 is not uniform with respect to the direction of thickness, judging from the laminated structure described above. For example, even if the pore diameter on the surface of the denture plate 4 is large, it is reduced inside the plate 4. The aforestated range of pore diameter of 0.1 to 500 $\mu$m is shown as the range of pore diameter varying in the direction of plate thickness described above making holding of liquid (saliva and food liquid) compatible with passage of the liquid. Viewed from a point of liquid holding alone, a relatively small pore diameter is desirable in the light of surface tension of liquid, but conversely, from a viewpoint of liquid passage, a larger diameter is desirable. The pore diameter thus has self-confronting demand on its formation. In the denture plate of the invention, when the surface pore diameter is relatively large (for example, 500 $\mu$m), the presence of a pore diameter of about 10 $\mu$m inside the thickness of the net assures holding the passage of liquid, and conversely when the diameter of surface pore is relatively small, formation of a large diameter pore with respect to the direction of thickness assures holding and passage of liquid. State differently, determination of the pore diameter in consideration of a dual point of holding and passage of liquid provides suitable selection from the aforestated range of 0.1 to 500 μm. When the liquid acts on the inside and outside of the denture plate 4, the liquid passes through the complicatedly curved pores 34 in the direction of thickness and flows over the inside and outside surfaces as shown in FIG. 8 and is substantially filled and held in each pore 34 by surface tension without bubbles being formed. Accordingly, when the denture plates 4 are put in the upper and lower jaws respectively, the plates are sucked and held firmly on the mucous membrane by the liquid. As well known, when masticatory pressure is applied to the denture plate 4 by bite occlustion, the plate facing the mucous membrane under the denture plate is placed under positive pressure, and in the case of the invention, the liquid in the oral cavity is transferred from the upside of the denture plate 4 to the underside of the plate and conversely the masticatory pressure is released to bring the underside of the plate 4 into negative pressure, whereupon the liquid is transferred from the underside to the upside of the denture plate 4, thus the liquid passing through the thickness of the plate 4 and making free communication between the oral cavity side and the mucous membrane side.

On the other hand, leavings of masticated food tend to pass from the surface of the denture plate 4 through the pores 34 into the inside of the plate, but as earlier stated, the pores 34 are curved with respect to the direction of thickness, so that the leavings are prevented from moving into the depths of the denture plate 4 by the warps 30 and wefts 31 present in the direction of thickness and stay in the surface portion of the plate. Accordingly, the denture plate of the invention makes it possible to efficiently remove the masticated food leavings by taking the denture out of the mouth and subjecting the surface of the plate 4 to suction or ultrasonic cleaning. Since the denture plate of the invention further contains numerous minute pores 34, it is also large in elastic deformation due to bite occlusion and provides a feeling of bite occlusion approximate to a natural feeling during mastication and in addition, the plate is reduced in weight over the portions corresponding to the pores 34, so that the user of the denture does not feel like waring artificial teeth but feels nices and refreshed. Furthermore, the user can not only enjoy a taste and a sense of temperature of food unlike when he wears a conventional denture in his mouth, but also is assured of maintaining the physiological function and health of the mucous membrane under the plate because the mucous membrane under the plate is supplied with oxygen and nutrient by the oral liquid. Sintering of the crossing portions 300 and 301 assures strength of the denture plate in the direction of thickness and extension of the plate and can strongly endure various kinds of repeated masticatory force. In the embodiment shown in FIGS. 1 and 2 as the denture of the invention having the denture plate of the kind described above is shown a full denture in which artificial teeth 2 are set in a plastic alveolar ridge 1 over the entire row of teeth and in which the entire circumferential edge of the denture plate 4 is moldedly jointed integral to the alveolar ridge 1 of resin. The structure of the full denture of the type described above is the same as a conventional one except the porous structure of the denture plate 4.

Figure 3:
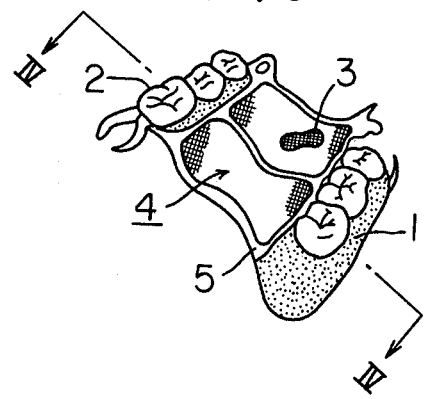
FIG. 3 is a perspective view of a partial denture of the upper jaw embodying the invention.
Figure 4:
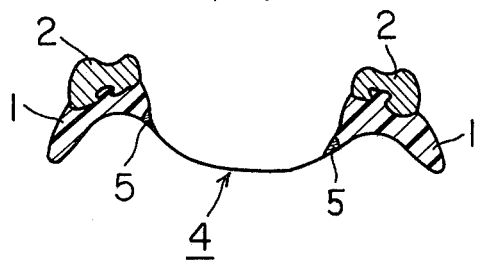
FIG. 4 is an enlarged sectional view taken along the line IV—IV of FIG. 3.

In the embodiment shown in FIGS. 3 and 4 is shown a partial denture, in which the numeral 5 designates a reinforcement frame. The entire margin of the denture plate 4 is moldedly jointed integral to the alveolar ridge 1 through the frame 5. This partial denture structure is also well known except that the denture plate 4 is of a porous structure.

The weave structure of the denture plate 4 permits free selection of any one such as Dutch weave, plain twilled weave in addition to the plain square weave in FIG. 7 and the twilled Dutch weave in FIG. 9. Since the case of the plaiin square weave, the square crossing the warps 30 and wefts 31 is slightly unsmooth to the palate and also the pores 34 produce a tendency to be rather large, which, in turn, produces a tendency of the leavings of masticated food to stay in the pores to thereby reduce that surface tension of the liquid in the pores by which to hold the leavings. In consideration of making the overlapping of the wefts 31 close and reducing the pores 34 in diameter, the use of twilled Dutch weave net on the outermost surface of the net, namely on the upside of the denture plate 4 alone and the use of plain square weave net on the outside of the net are desirable from the viewpoint of making taste of food pleasant to the palate, making the food leavings restricted in their entrance into the innermost surface layer of the denture plate, and increasing the liquid holding property of the denture plate. Those ordinarily skilled in the art will find it easy to select a suitable combination of layers, judging from the shape of texture, such as plain twilled weave, Dutch weave.

Summing up the aforestated advantages brought about by the porous structure of the denture plate of the invention, they are provided in the substantial increase in aptitude of denture in that, since saliva and food liquid are carried freely through the upside and underside of the denture plate, suction and retention of a denture in the oral cavity are possible with no possibility of unintended separation of the denture from the mouth; that the supply of oxygen and nutrient to the mucous membrane under the denture plate by such passage of saliva and food liquid is conductive to the maintainence of health; that the denture makes is possible to have a sense of taste and feel a temperature of food in the state approximate to natural mastication; that, because the denture plate is lightweight and large in elastic deformation with respect to bite occlusion, a feeling resulting from the denture put in and a feeling of bite occlusion are natural and agreeable; that it sufficiently resists various types of biting force; that it prevents the leavings of masticated food from moving into the depths of the denture plate and thus makes it easy to remove the leavings by cleaning; and the like.

We claim:

1. A denture having a porous metal gauze as a denture plate, said porous metal gauze being formed of plural wire nets with a straight wire used as warps and wefts, said nets being laid one over another in layers so as to stagger the meshes thereof with respect to the direction of thickness and to bring the warps and wefts into a parallel relation with each other with respect to the direction of extent, said layered nets being pressed in the direction of thickness, and the crossing portions of said warps and wefts in the same plane and the crossing portions of said warps and wefts in contact with each other in the direction of thickness being sintered to form a plurality of minute and complicatedly curved pores in said porous metal gauze.

2. A denture according to claim 1 having said porous metal gauze in single as a denture plate for a full denture.

3. A denture according to claim 1 having said porous metal gauze as a denture plate for a partial denture by joining a reinforcement frame to the porous metal gauze.

4. A denture according to claim 1 wherein said nets to be laid one over another in layers are wholly of plain square weave net.

5. A denture according to claim 1 wherein out of the wire nets to be laid one over another in layers that net of the denture plate facing the oral cavity side is of twilled Dutch weave net and the nets in the other layered parts are of plain square weave.

6. A denture according to claim 1 wherein the wire net is any one selected from titanium alloy net, cobalt chromium alloy net, and stainless steel net, and has a width of 100 to 1000 $\mu$m and a pore diameter of 0.1 to 500 $\mu$m, preferably 10 $\mu$m, after pressing and sintering.

7. A denture according to claim 1 wherein the pores in the net are 20 to 70% in porosity.

* * * * *